(12) United States Patent
Ingram et al.

(10) Patent No.: US 9,757,522 B2
(45) Date of Patent: *Sep. 12, 2017

(54) ENTERAL SYRINGE

(71) Applicant: NEOMED, INC., Woodstock, GA (US)

(72) Inventors: Aaron N. Ingram, Canton, GA (US); Benjamin Martin Davis, Woodstock, GA (US); Anthony C. Lair, Alpharetta, GA (US); Mark Martin Costello, County Mayo (IE); Tony Doherty, County Mayo (IE)

(73) Assignee: NEOMED, INC., Woodstock, GA (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/614,156

(22) Filed: Feb. 4, 2015

(65) Prior Publication Data

US 2015/0148753 A1 May 28, 2015

Related U.S. Application Data

(60) Division of application No. 13/231,185, filed on Sep. 13, 2011, now Pat. No. 8,992,488, which is a
(Continued)

(51) Int. Cl.
*A61M 5/315* (2006.01)
*A61M 5/31* (2006.01)
(Continued)

(52) U.S. Cl.
CPC .......... *A61M 5/3129* (2013.01); *A61J 7/0053* (2013.01); *A61M 5/008* (2013.01);
(Continued)

(58) Field of Classification Search
CPC ...... A61M 2005/3123; A61M 5/31511; A61M 5/31513
(Continued)

(56) References Cited

U.S. PATENT DOCUMENTS 3,885,562 A 5/1975 Lampkin
5,279,566 A 1/1994 Kline, Jr. et al.
(Continued)

FOREIGN PATENT DOCUMENTS

DE 2108381 B2 8/1972
EP 1110568 A2 6/2001
(Continued)

OTHER PUBLICATIONS

NeoMed Enteral Syringe; 2007; 8 pgs.
Partial International Search Report for PCT/US2011/051338; Dec. 14, 2011; 2 pgs.

*Primary Examiner* — Kevin C Sirmons
*Assistant Examiner* — Deanna K Hall
(74) *Attorney, Agent, or Firm* — Gardner Groff Greenwald & Villanueva, PC

(57) ABSTRACT

A syringe having a syringe body defining an elongate cavity therein with a non-circular internal cross-sectional profile, and a syringe plunger operable to selectively travel within the hollow cavity with a non-circular external cross-sectional profile that substantially mirrors the syringe body's internal cross-sectional profile for mating engagement thereof. The enteral syringe may also have venting features and support features for hanging from a support structure.

21 Claims, 19 Drawing Sheets

Related U.S. Application Data continuation-in-part of application No. 29/380,242, filed on Dec. 2, 2010, now Pat. No. Des. 654,585.

(60) Provisional application No. 61/382,720, filed on Sep. 14, 2010, provisional application No. 61/418,963, filed on Dec. 2, 2010.

(51) Int. Cl.
  *A61M 5/145* (2006.01)
  *A61J 7/00* (2006.01)
  *A61M 5/00* (2006.01)

(52) U.S. Cl.
  CPC ........ *A61M 5/1452* (2013.01); *A61M 5/1456* (2013.01); *A61M 5/31511* (2013.01); *A61M 5/31513* (2013.01); *A61M 2005/3123* (2013.01)

(58) Field of Classification Search
  USPC .................................................. 604/218, 227
  See application file for complete search history.

(56) References Cited

U.S. PATENT DOCUMENTS

| | | |
|---|---|---|
| 5,843,042 A | 12/1998 | Ren |
| D654,584 S * | 2/2012 | Costello ........................ D24/114 |
| D654,585 S * | 2/2012 | Costello ........................ D24/114 |
| 8,540,683 B2 | 9/2013 | Williams, Jr. et al. |
| 2006/0264824 A1 | 11/2006 | Swisher, III |

FOREIGN PATENT DOCUMENTS

| | | |
|---|---|---|
| EP | 1980282 A1 | 10/2008 |
| FR | 1126718 | 6/1955 |
| WO | 2011026156 A1 | 3/2011 |

\* cited by examiner

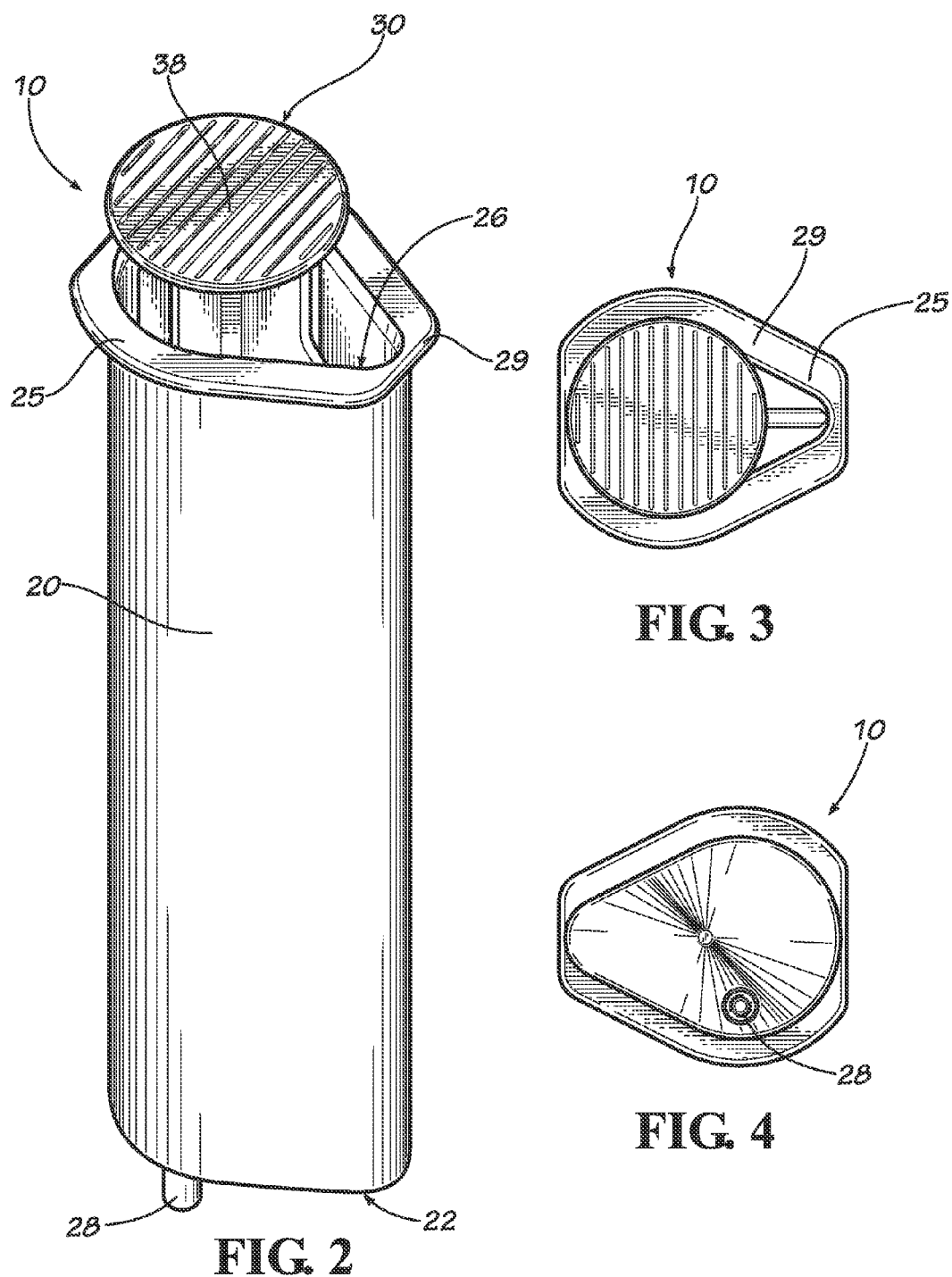

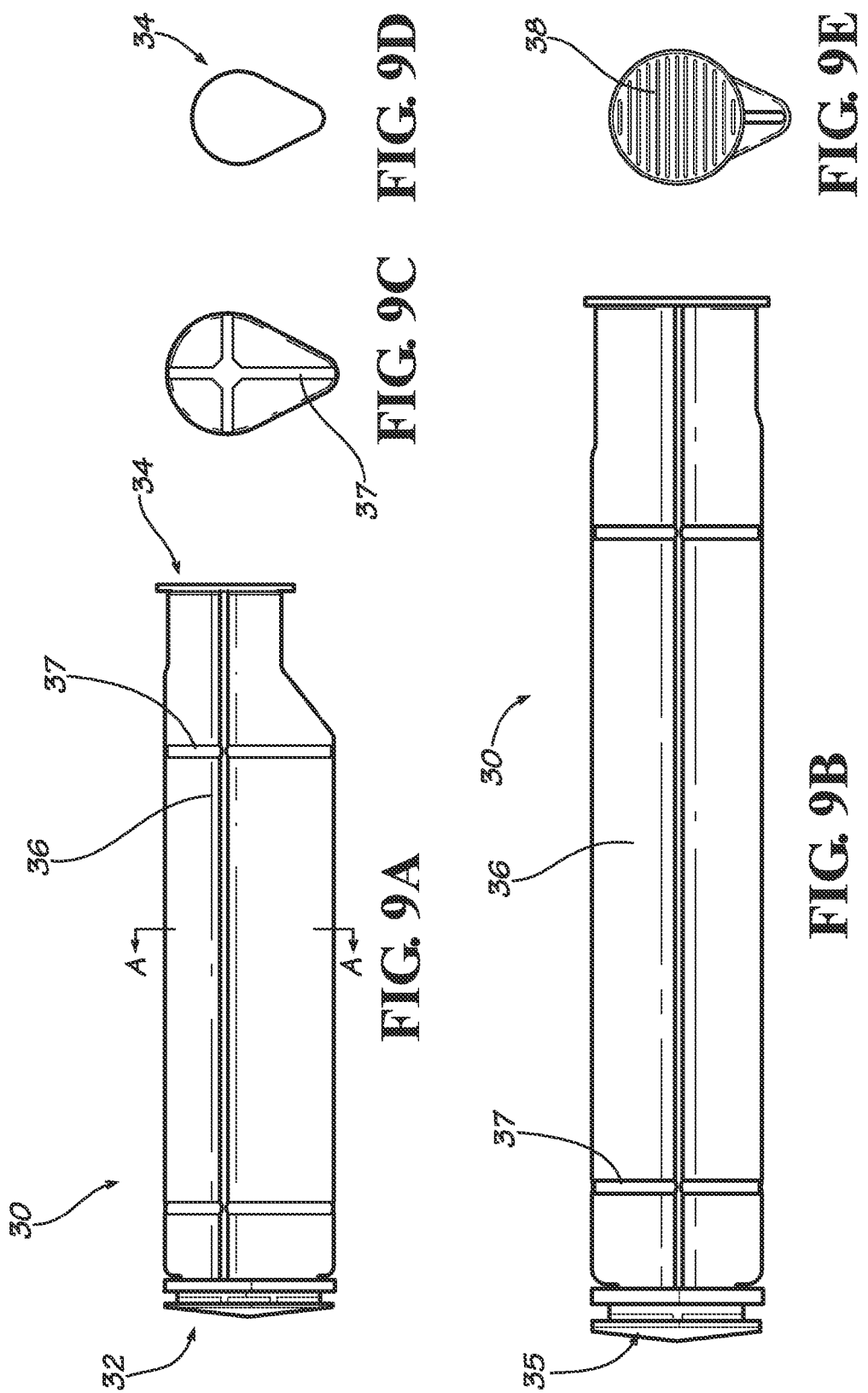

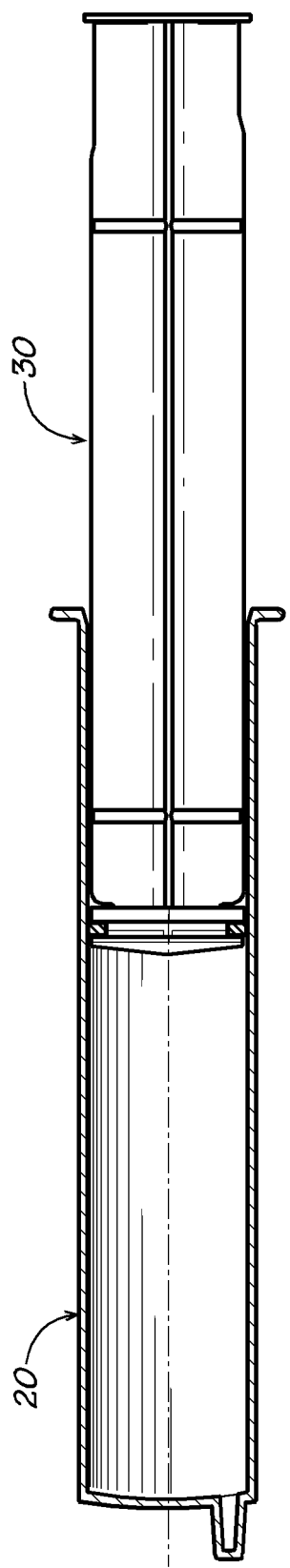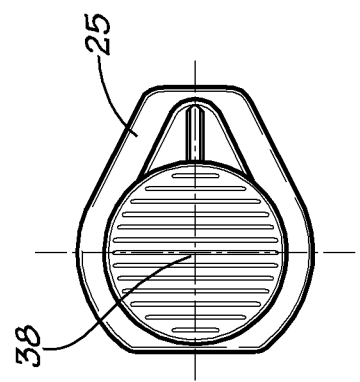
FIG. 12A
FIG. 12B

FIG. 16A    FIG. 16B

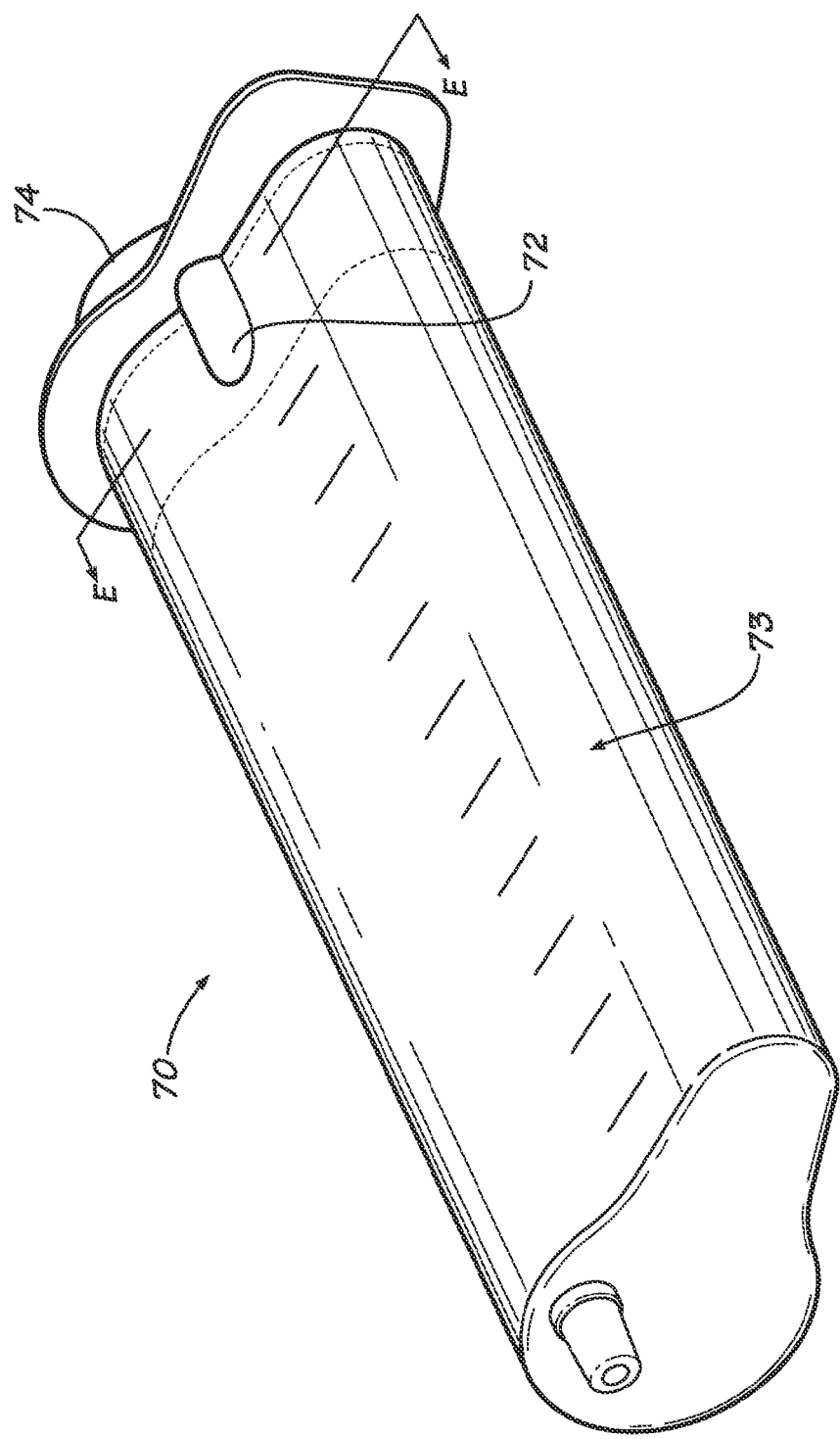

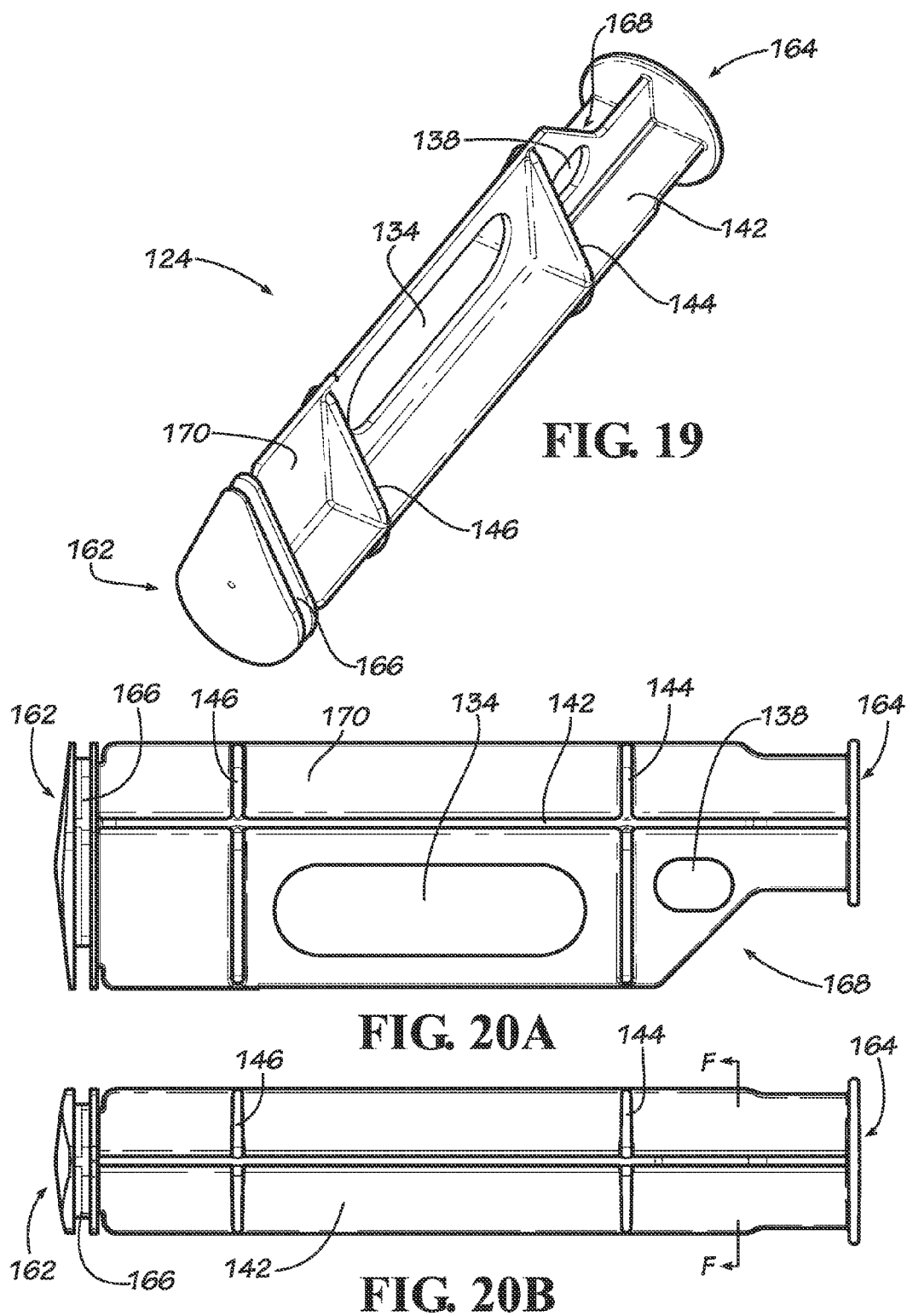

ENTERAL SYRINGE

CROSS-REFERENCE TO RELATED APPLICATION

This application is a divisional of U.S. Non-Provisional patent application Ser. No. 13/231,185 filed Sep. 13, 2011, which claims the benefit of U.S. Provisional Patent Application Ser. No. 61/382,720 filed Sep. 14, 2010, and of U.S. Provisional Patent Application Ser. No. 61/418,963 filed Dec. 2, 2010; U.S. Non-Provisional patent application Ser. No. 13/231,185 filed Sep. 13, 2011 is a continuation-in-part of and claims priority to U.S. Design patent application Ser. No. 29/380,242, filed Dec. 2, 2010; the entireties of which are hereby incorporated herein by reference for all purposes.

TECHNICAL FIELD

The present invention relates generally to the field of containment and dispensing of fluids, and more particularly to a containment and dispensing system for biological fluids such as breast milk, and/or other dietary or medicinal materials.

BACKGROUND OF THE INVENTION

Syringe pumps, or drivers, are small infusion pumps used to gradually administer small amounts of fluid to a patient. When administering drugs (e.g. painkillers, antiemetics, etc.) syringe pumps prevent periods during which the medication levels in the blood are too high or too low, and prevent a patient from having to repeatedly take tablets or pills. Additionally, syringe pumps are effective at administering medication over many minutes or hours and often reduce errors by caretakers.

One particular use of syringe pumps is in the field of enteral feeding administration. For example, syringe pumps are especially useful for the administration of breast milk (or suitable substitutes) in the care and treatment of neonatal children. An example of a syringe pump and syringe used for neonatal enteral feeding is shown in FIG. 1, which depicts a Medfusion® brand (Model No. 3500) syringe pump. One drawback to known syringe pumps/syringes is that known pumps have a very limited range of syringe sizes (diameter, height, length, etc.) and shapes that they will receive and operate in conjunction therewith. In particular, commercially-known pumps typically accept round syringes that have a maximum volume of about 75 mL. As such, users wishing to dispense more than 75 mL of fluid in a single setting must monitor the pump and change the syringe(s) out as needed. Accordingly, it can be seen that needs exist for syringes that are compatible with known syringe pumps but have larger capacities to permit longer enteral infusion sessions.

Alternatively, enteral syringes can be used with gravity feed systems, for example, when administering nutrients and/or medications to a neonatal patient. When administering fluids to a patient via a gravity-feed system, the syringe plunger is typically removed from the syringe body to prevent a vacuum from developing inside the syringe as the fluid leaves the syringe and enters the patient. The removal of the plunger from the syringe body is often seen as a drawback to this process and requires that a user take special care in storing the plunger while the syringe is being utilized. In the past, users have strapped the plunger to the syringe body or otherwise stored the plunger on a sterile tray or other location to avoid permanently separating these components. Additionally, removing the plunger from the syringe body can expose the contents of the syringe to unwanted pathogens, dust or other foreign matter, which can be harmful to a patient. Thus, it can be seen that needs exist for an improved syringe for fluid delivery.

When administering fluids to a patient, the plunger must be removed from the syringe body to prevent a vacuum from developing inside the syringe as the fluid leaves the syringe and enters the patient. The removal of the plunger from the syringe body is often seen as a drawback to this process and requires that a user take special care in storing the plunger while the syringe is being utilized. In the past, users have strapped the plunger to the syringe body or otherwise stored the same on a sterile tray or other location to avoid permanently separating these components. Additionally, removing the plunger from the syringe body can expose the contents of the syringe to unwanted pathogens or other foreign matter, which can be harmful to a patient. Thus, it can be seen that needs exist for an enteral syringe that prevents a vacuum from developing within the syringe during use, while permitting a user to leave the plunger within the syringe body at all times during such use.

It is to the provision of improved devices and methods of fluid delivery meeting these needs and others that the present invention is primarily directed.

SUMMARY OF THE INVENTION

In example embodiments, the present invention provides improved devices and methods to administer fluids to a patient.

In a first aspect, the present invention relates to an enteral syringe for use with a syringe pump having an elongated body and a plunger. The elongated body includes a first non-circular cross-section and a hollow cavity therein. The plunger includes a second non-circular cross-section that substantially mirrors the first non-circular cross-section and is operable to travel within the hollow cavity. Optionally, the first and second cross-sections are tear-drop shaped or key-way shaped to accommodate more fluid than a circular cross-section.

In a second aspect, the present invention relates to a self-venting enteral syringe that includes a syringe body having a hollow internal cavity therein and at least one vent extending from the hollow cavity to an outside surface of the syringe body. The enteral syringe also includes a plunger operable to selectively travel within the hollow cavity.

In a third aspect, the present invention relates to a syringe that includes a barrel defining an interior chamber for receiving a fluid, and a discharge port for discharging the fluid therethrough. The syringe also includes a plunger adapted to slide inwardly and outwardly within the barrel. The plunger has a seal for sealing engagement with an interior surface of the barrel. The syringe also has at least one support feature for hanging the syringe from a support structure.

In a fourth aspect, the present invention relates to a method of delivery of fluid from a syringe. The method includes hanging the syringe from a support by engagement of the support with a support feature of the syringe and delivering fluid from a discharge port of the syringe.

In a fifth aspect, the present invention relates to an enteral syringe that includes an elongated body having and a hollow cavity therein and at least one vent extending from the hollow cavity to an outside surface of the syringe body. The elongated body has a first non-circular cross-section. The enteral syringe also includes a plunger operable to selectively travel within the hollow cavity. The plunger has a second non-circular cross-section that substantially mirrors the first non-circular cross-section. The enteral syringe also has at least one support feature for hanging the syringe from a support structure.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 2 is a perspective view of an enteral syringe according to a first example embodiment of the present invention.

FIG. 3 is a top view of the enteral syringe of FIG. 2.

FIG. 4 is a bottom view of the enteral syringe of FIG. 2.

FIG. 9A is a side view of a first example embodiment plunger that can be inserted into a body of an enteral syringe.

FIG. 9B is a bottom view of the plunger of FIG. 9A.

FIG. 9C is a cross-sectional view of the plunger of FIG. 9A taken at line A-A.

FIG. 9D is a bottom view of the plunger of FIG. 9A.

FIG. 9E is a top view of the plunger of FIG. 9A.

FIG. 12A is a top cross-sectional side view of the enteral syringe of FIG. 2, shown with the plunger in a retracted state from the body.

FIG. 12B is a top view of the enteral syringe of FIG. 12A.

FIG. 16A is cross-sectional side view of the enteral syringe of FIG. 15A, shown with the plunger in a first position.

FIG. 16B is cross-sectional side view of the enteral syringe of FIG. 15A, shown with the plunger in a second position.

FIG. 18A is a perspective view of an enteral syringe according to a fourth example embodiment of the present invention.

FIG. 19 is a perspective view of a second example embodiment plunger that can be inserted into an enteral syringe body.

FIG. 20A is a side view of the plunger of FIG. 19.

FIG. 20B is a top view of the plunger of FIG. 19.

DETAILED DESCRIPTION OF EXAMPLE EMBODIMENTS

Figure 1:
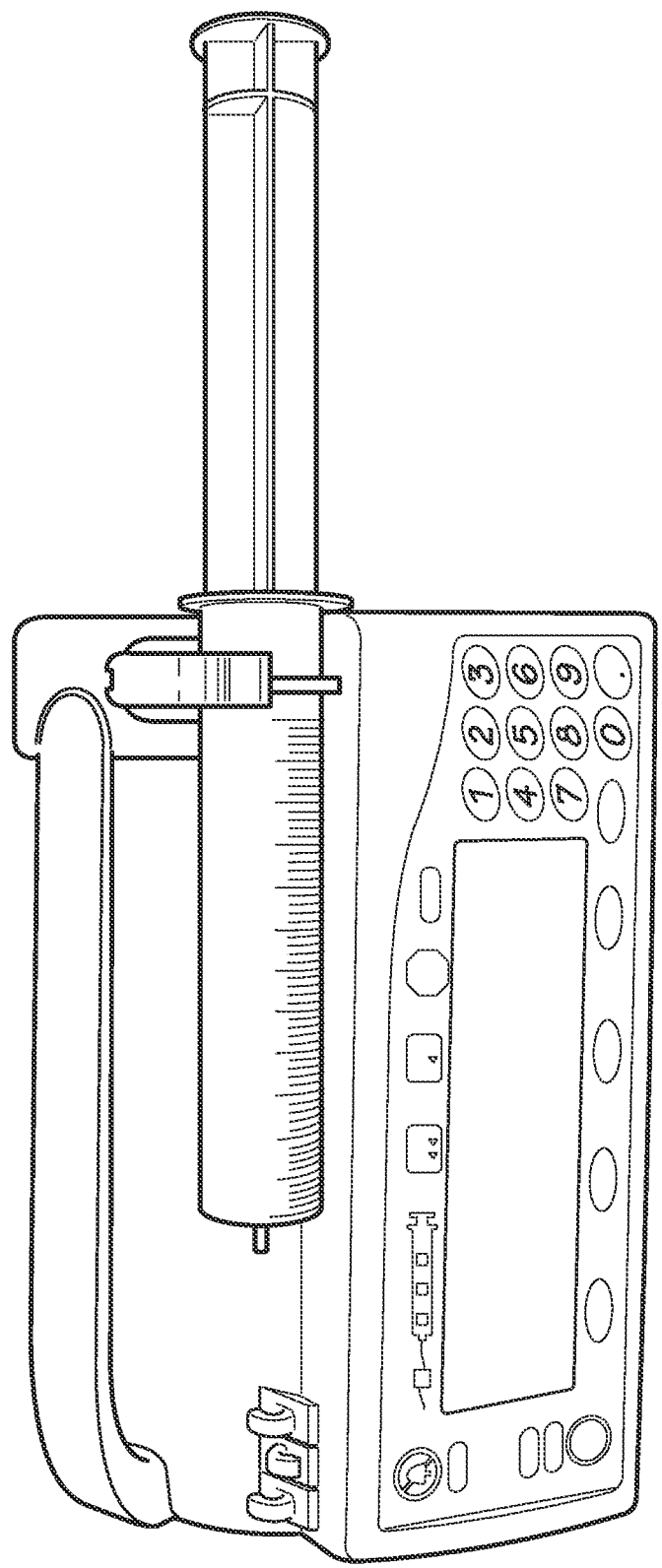
FIG. 1 is a perspective view of an enteral syringe and syringe pump of known form.
Figure 5:
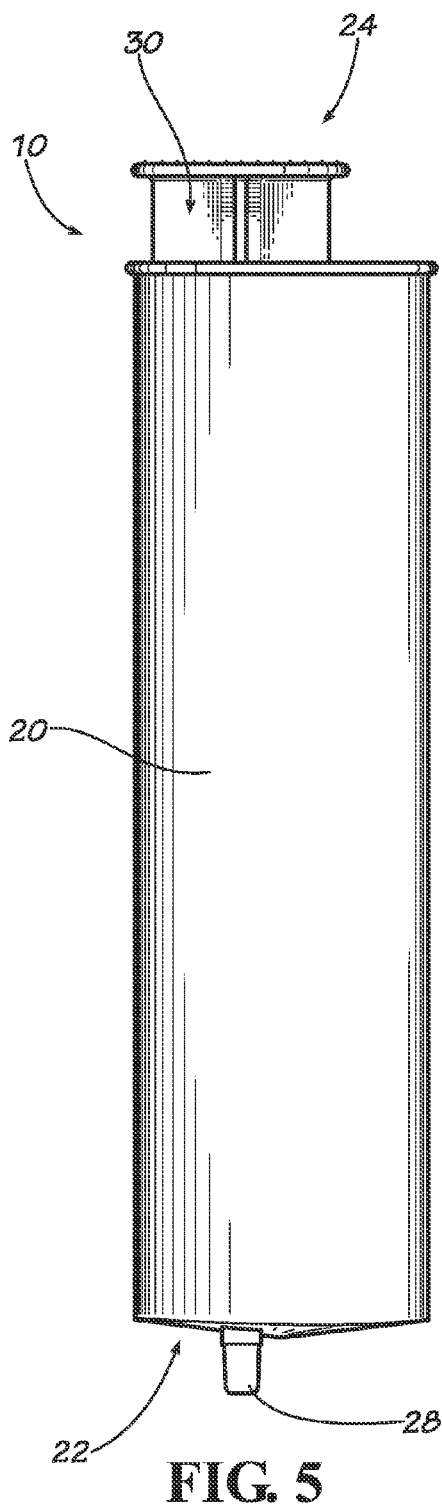
FIG. 5 is a first side view of the enteral syringe of FIG. 2.
Figure 6:
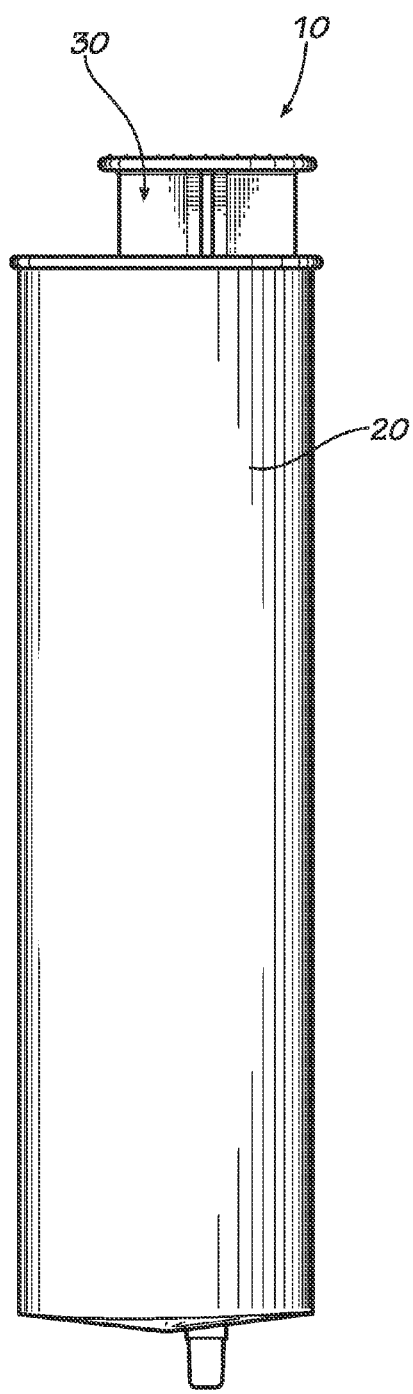
FIG. 6 is a second side view of the enteral syringe of FIG. 2.
Figure 7:
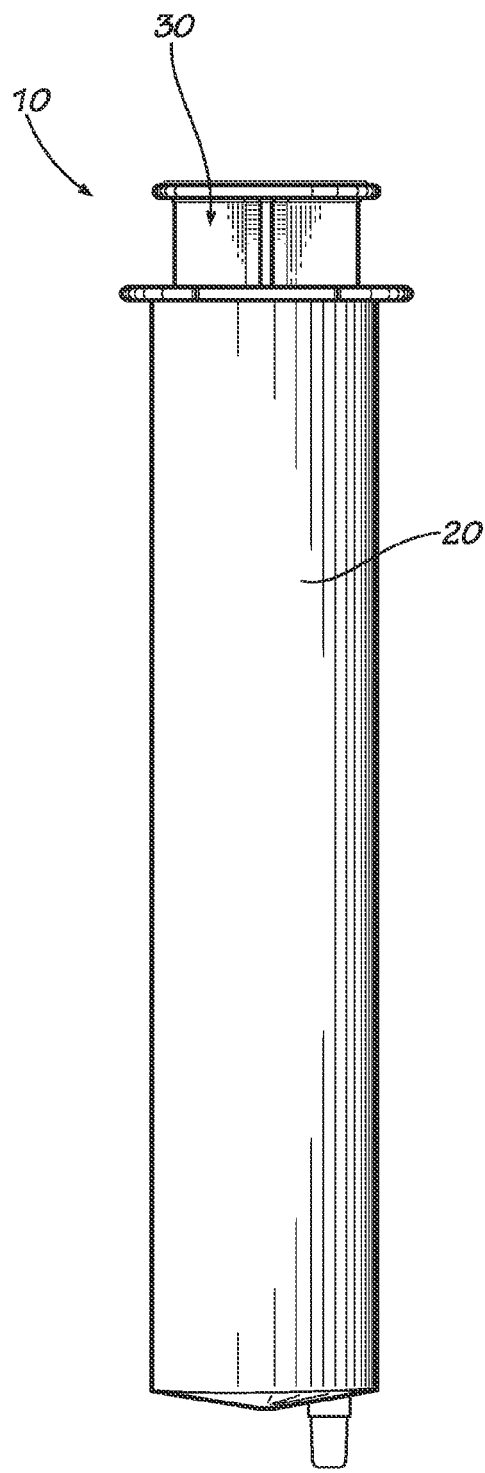
FIG. 7 is a back view of the enteral syringe of FIG. 2.
Figure 8:
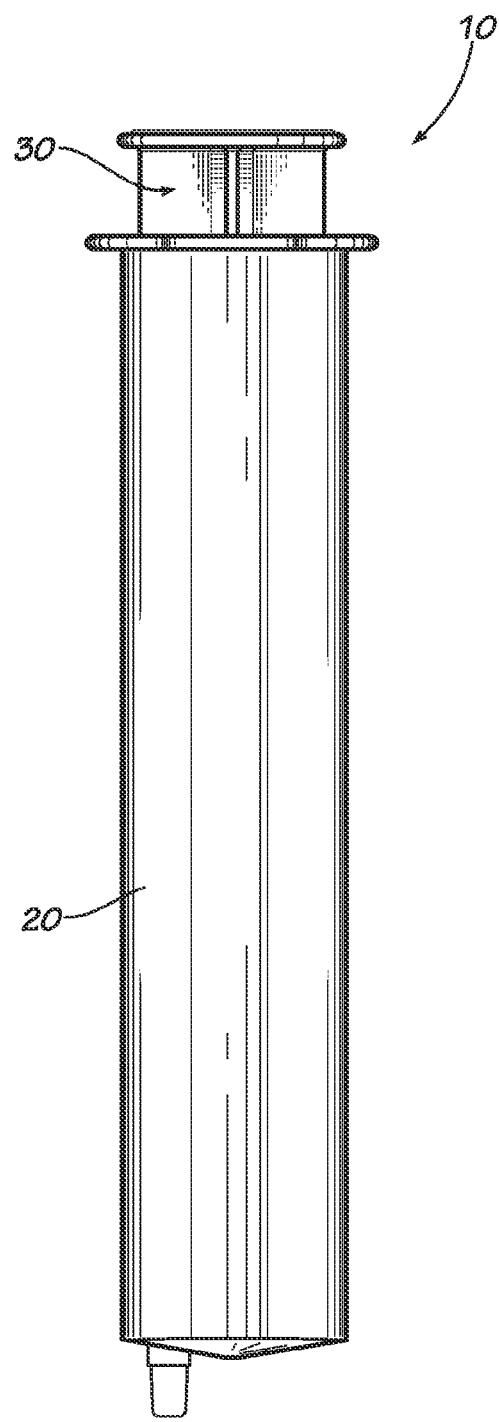
FIG. 8 is a front view of the enteral syringe of FIG. 2.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 2-8 depict an improved syringe 10 according to a first example embodiment of the present invention. As briefly discussed above, known syringe pumps (such as the Mefusion® brand syringe pump) only accept syringes that incorporate a particular set of parameters. As a result, known syringes are traditionally circular in cross-section to fit within these parameters. Thus, in the past, syringes for use with traditional syringe pumps have been limited in their capacities to hold fluids. For example, known syringes have a maximum capacity of only about 75 mL. In contrast, the improved syringes according to example embodiments of the present invention utilize a non-circular cross-sectional shape, such as a tear-drop shape or key-way shape, to expand their capacity over known syringes—while still maintaining compatibility with typical known pumps. In effect, the syringe of the present invention can be used with various known syringe pumps, such as the Medfusion® brand pump depicted in FIG. 1, and is capable of storing and administering significantly more fluid than known syringes.

In example embodiments, the syringe includes an elongated body. The cross-section of the syringe is preferably non-symmetrical along both axes, as exemplified in the embodiment shown in FIG. 4. In other example embodiments, the cross-section of the syringe is non-symmetrical along only one axis. As shown, an example syringe 10 of the present invention includes an elongated body 20 having a non-circular substantially tear-drop shaped cross-section and at least one correspondingly-shaped plunger 30 for slidable insertion therein. Because of the unique tear-drop shaped cross-section, the syringe 10 of the present invention is capable of storing and administering over about 100 mL of fluid in one setting while still maintaining compatibility with the predetermined parameters of known syringe pumps. In alternate embodiments, the syringe 10 is capable of storing over about 80 mL, and more preferably over about 90 mL of fluid(s).

As shown, the elongate body 20 includes a first distal end 22 that is operable to releasably couple with a syringe pump and a second proximal end 24 for receiving the at least one plunger 30 therein. At the proximal end 24, the syringe body 20 also includes a flange 25 to provide a finger hold to permit manual operation by a user as is typical with known syringes or to engage a syringe pump. While the flange 25 depicted in FIGS. 2-8 includes a substantially tear-drop shaped rim 29 that is truncated at each end, other embodiments can include a rim that is key-way shaped, circular, elliptical, having a constant width, or can be otherwise shaped as desired. An elongate cavity 26 generally extends within the body 20 along the length of the same from the proximal end 24 towards the distal end 22. In preferred example embodiments, the cavity 26 mirrors, or substantially mirrors, the cross-section of the syringe body 20 providing a substantially constant outer-wall thickness of the same. As shown, the distal end 22 can include a semi-pointed face. At the distal end 22 of the syringe body, the cavity 26 terminates and at least one tip or nipple 28 is provided for insertion into a suitable syringe pump (not shown) and/or enteral feeding tube for delivery of the fluid contents contained therein. In preferred example embodiments, the tip 28 is sized and shaped to correspond to a Medfusion® branded syringe pump, but can be sized and shaped as desired to operate with other syringe pumps. In depicted embodiments, the tip 28 is located away from the cross-sectional center of gravity, and more preferably near the perimeter of the syringe body distal end 22.

As intended, when the syringe 10 is oriented for use within a suitable syringe pump the tip 28 is preferably positioned above the cross-sectional center of gravity. It has been found that colostrum contained within breast milk rises to the top of the syringe, and thus, locating the tip 28 above the center of gravity, and more preferably at the top of the distal end 22 perimeter, permits the controlled feeding of colostrum during a particular enteral feeding session. The tip 28 can also include a removable cap for selectively covering the tip 28 as desired. In alternative embodiments, the tip 28 can be located as desired to cooperate with various syringe pumps. In other alternative embodiments, the syringe 10 can include two or more tips 28 to permit operational flexibility with multiple brands/units of syringe pumps. In still other embodiments, the syringe 10 can include three or more tips 28 or the tip(s) can be interchangeable.

Figure 13A:
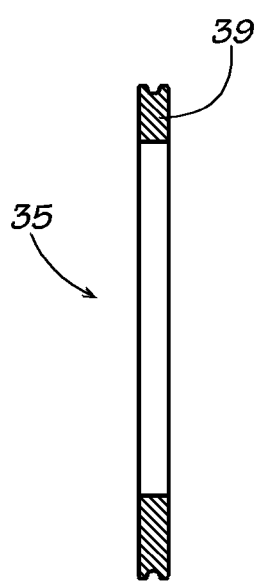
FIG. 13A is a cross-sectional side view of a gasket head seal for use with the plunger of FIG. 9A.
Figure 13B:
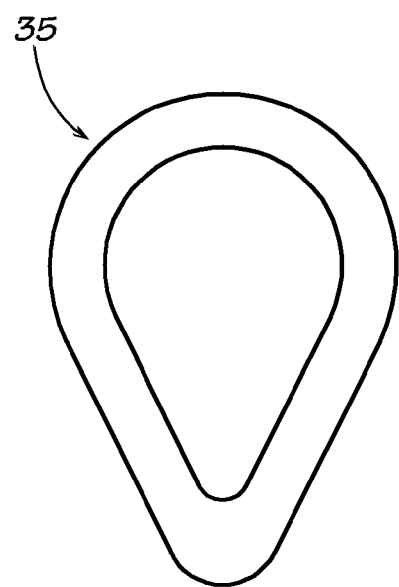
FIG. 13B is a top view of the seal of FIG. 13A.
Figure 14A:
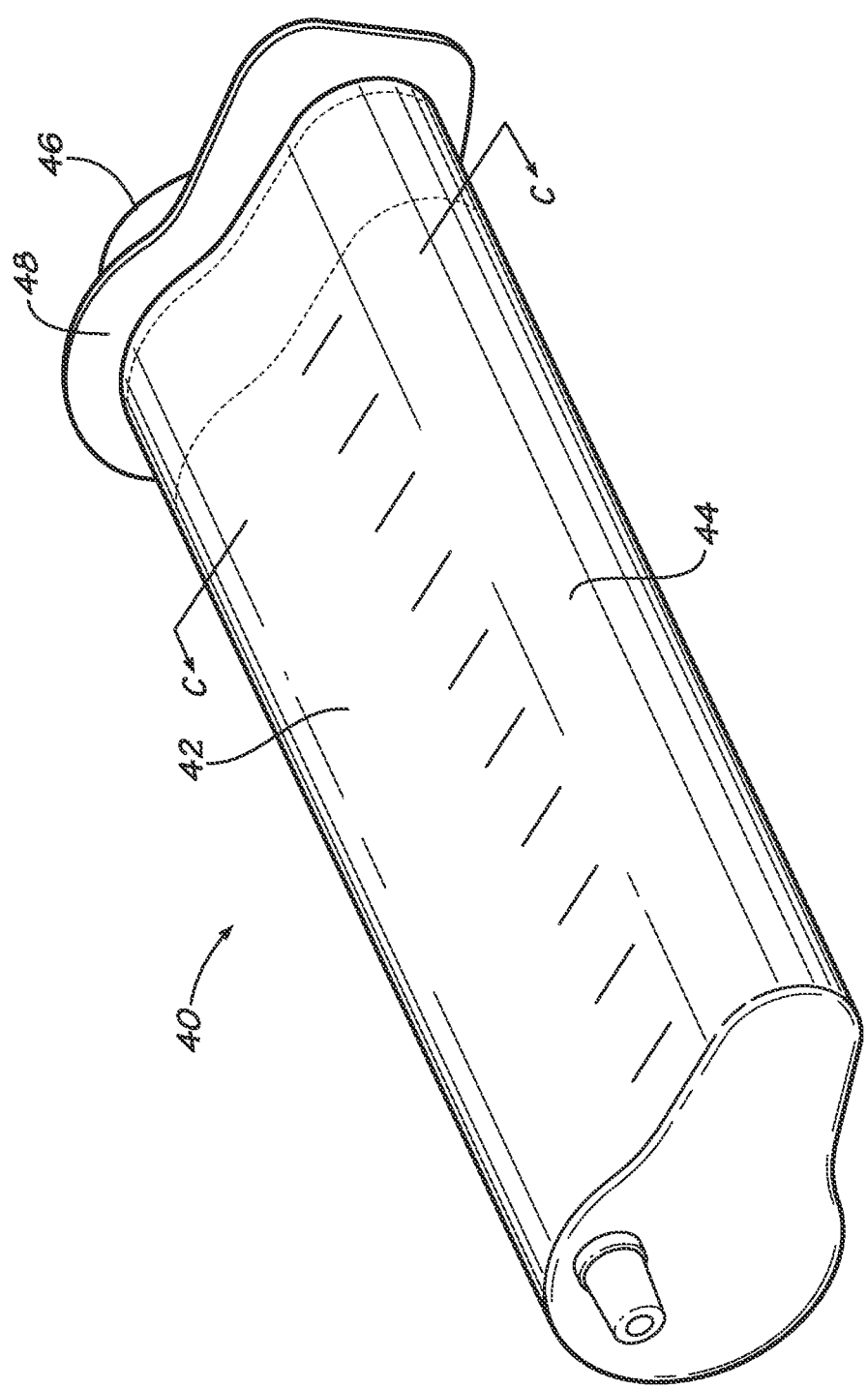
FIG. 14A is a perspective view of an enteral syringe according to a second example embodiment of the present invention.
Figure 14B:
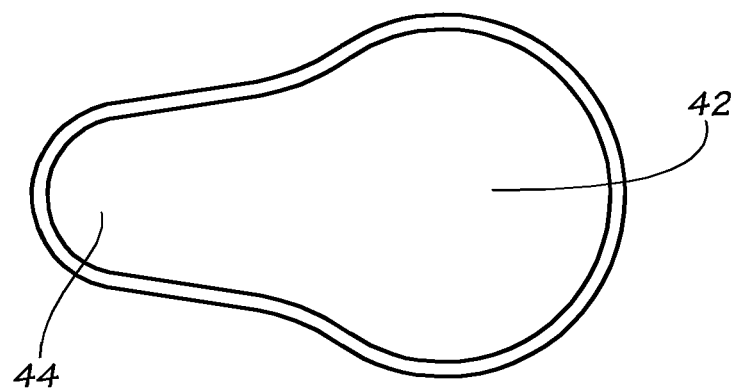
FIG. 14B is a cross-sectional view of the body of the enteral syringe of FIG. 14A taken at line C-C.
Figure 14C:
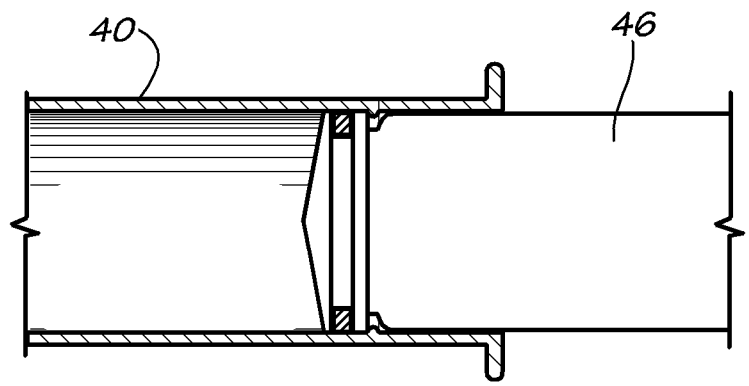
FIGS. 14C-14D are cross-sectional side views of the enteral syringe of FIG. 14A.
Figure 14D:
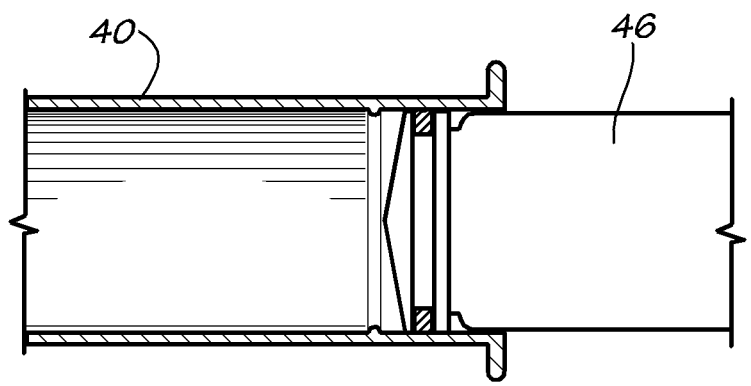
Figure 15A:
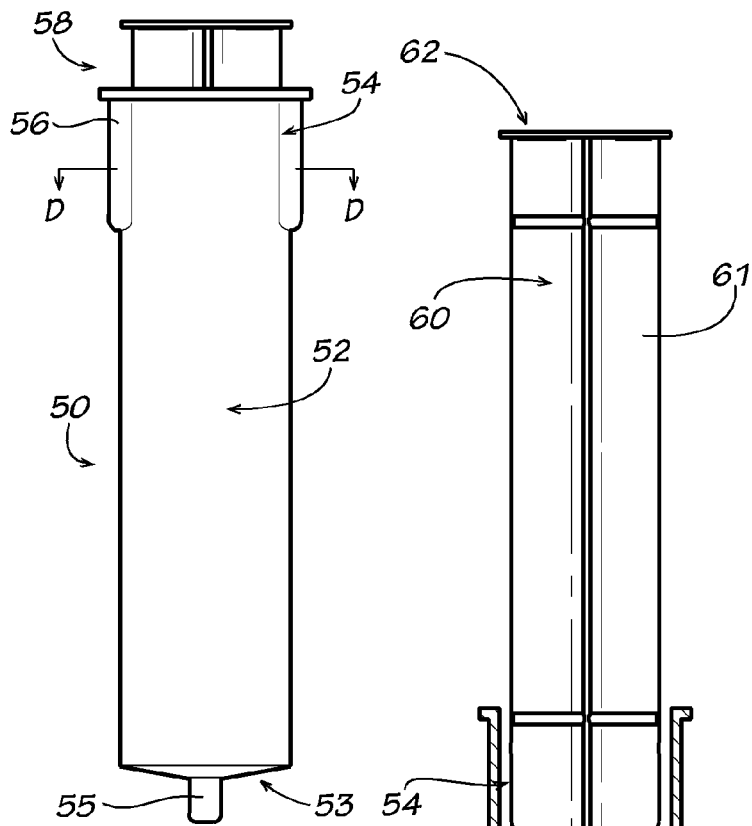
FIG. 15A is a side view of an enteral syringe according to a third example embodiment of the present invention.
Figure 15B:
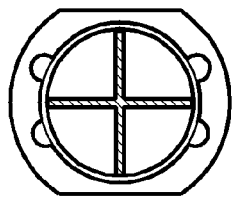
FIG. 15B is a cross-section view of the enteral syringe of FIG. 15A taken at lines A-A.
Figure 15C:
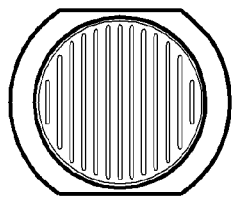
FIG. 15C is a top view of the enteral syringe of FIG. 15A.
Figure 17A:
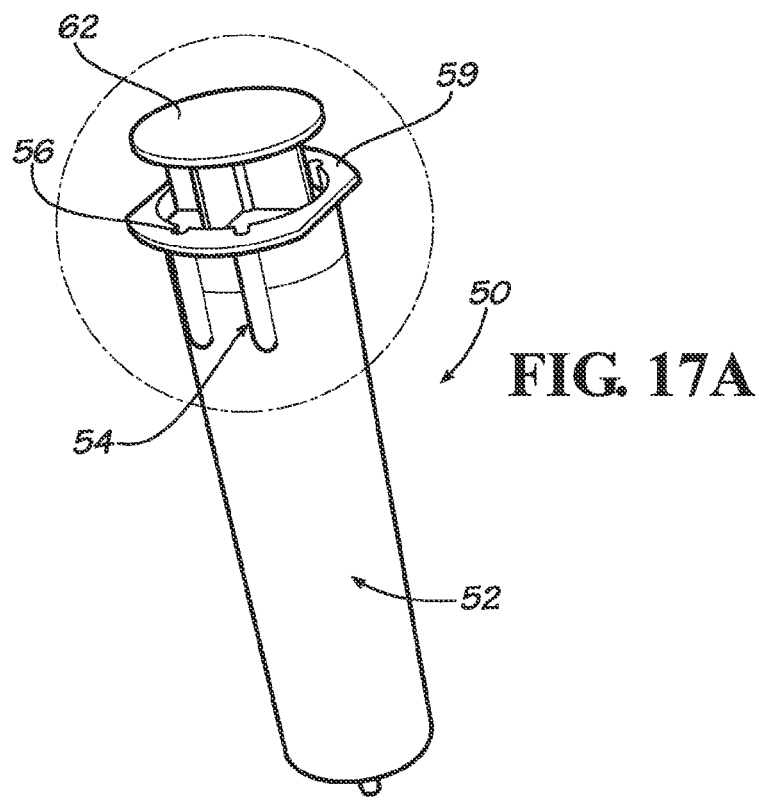
FIG. 17A is a perspective view of the enteral syringe of FIG. 15A.
Figure 17B:
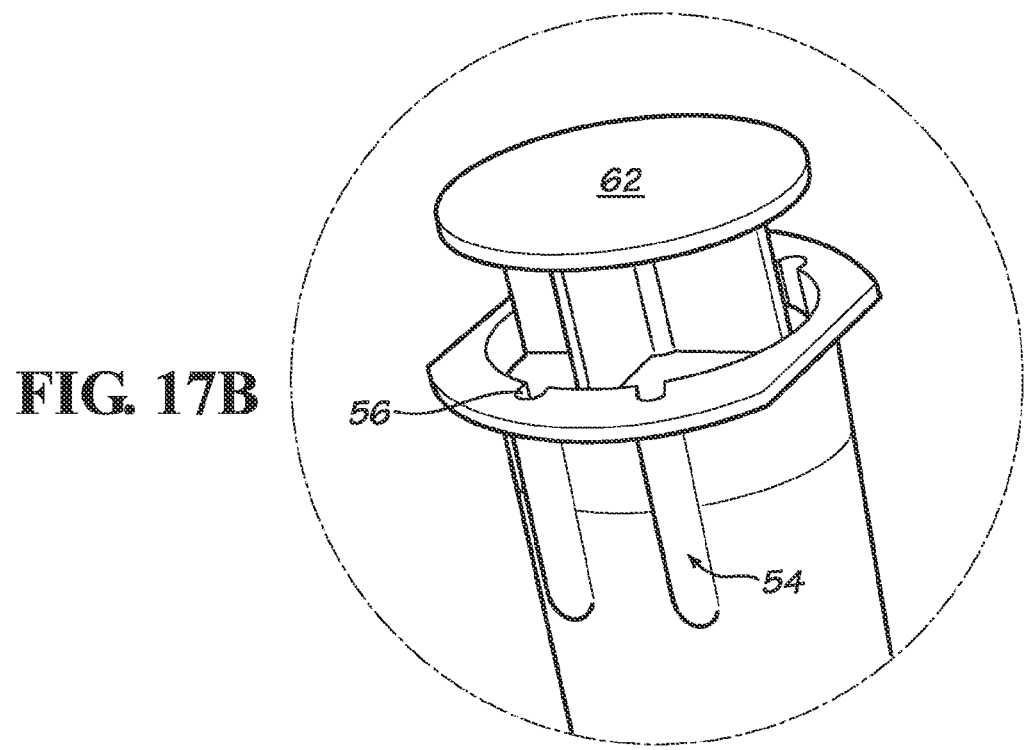
FIG. 17B is a close up perspective view of the enteral syringe of FIG. 15A.
Figure 18B:
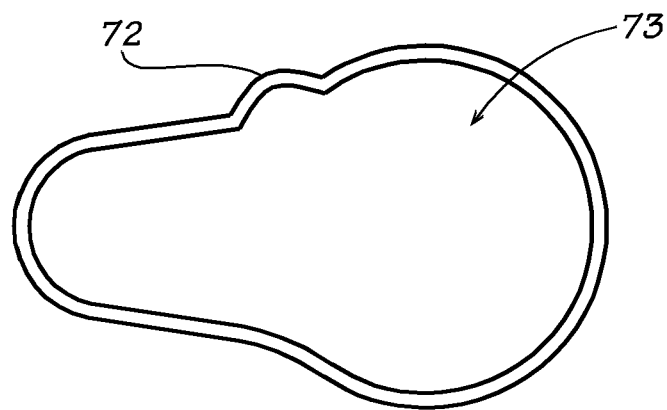
FIG. 18B is a longitudinal cross-section view of the enteral syringe of FIG. 18A taken at line D-D.
Figure 18C:
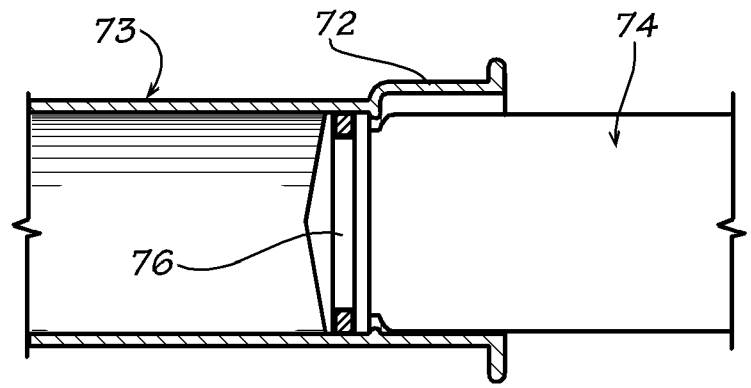
FIG. 18C is an isolated cross-sectional side view of the enteral syringe of FIG. 18A, shown with the plunger in a first position.
Figure 18D:
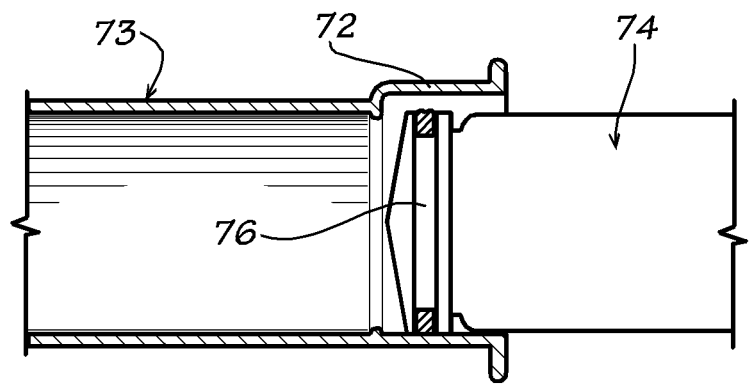
FIG. 18D is an isolated cross-sectional side view of the enteral syringe of FIG. 18A, shown with the plunger in a second position.
Figure 21A:
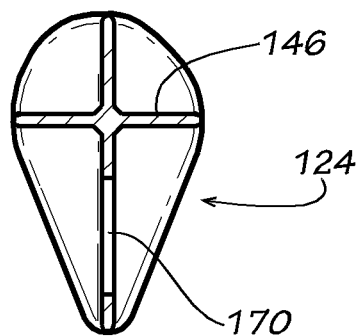
FIG. 21A is a cross-sectional view of the plunger of FIG. 20A taken at section E-E.
Figure 21B:
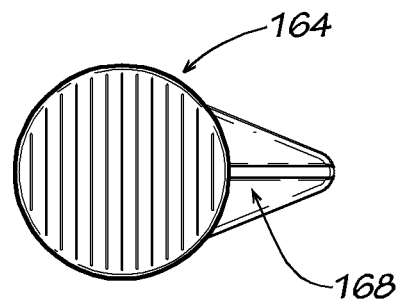
FIG. 21B is a top view of the plunger of FIG. 19.
Figure 21C:
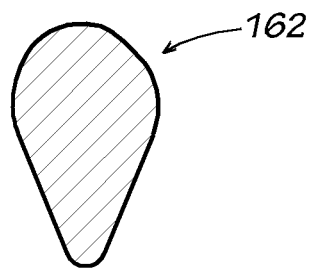
FIG. 21C is a bottom view of the plunger of FIG. 19.

FIGS. 9A-9E depict the example plunger 30 in greater detail. The plunger includes a first distal end 32 and second proximal end 34. The distal end 32 comprises a sealing head 35 for tightly engaging the inner wall of the body cavity 26. As shown in FIG. 9D, the sealing head and/or gasket 35 substantially mirrors the cross-section and diameter of the cavity 26 to provide an appropriate seal between the head and the cavity, and in example embodiments, is substantially tear-drop shaped as shown. As depicted in FIGS. 13A-13B, the gasket 35 is shown to include a sealing material 39 that creates a seal between the gasket and the inner wall of the body 20. As shown, the distal end 32 can include a slightly pointed face corresponding with the pointed face of the body distal end 22. The plunger 30 also includes a plunger body 36 that comprises at least one, and preferably two or more ribs 37 that also substantially mirror the cross-section and diameter of the cavity 26. As the plunger 30 is selectively inserted into the cavity 36 of the syringe body 20 and travels therein during use, the ribs 37 operate to keep the plunger 30 aligned within the cavity 26 and prevent the plunger from tipping within the same. As such, the ribs 37 help maintain a good seal between the plunger head 35 and the wall of the cavity 26. At the proximal end 34 the plunger 30 includes a contact face 38 to engage a corresponding depressor of a syringe pump (or permit user manipulation for hand operation). In example embodiments, the contact face 38 is circular in shape. Alternatively, the contact face 38 can be any shape as desired.

Figure 10A:
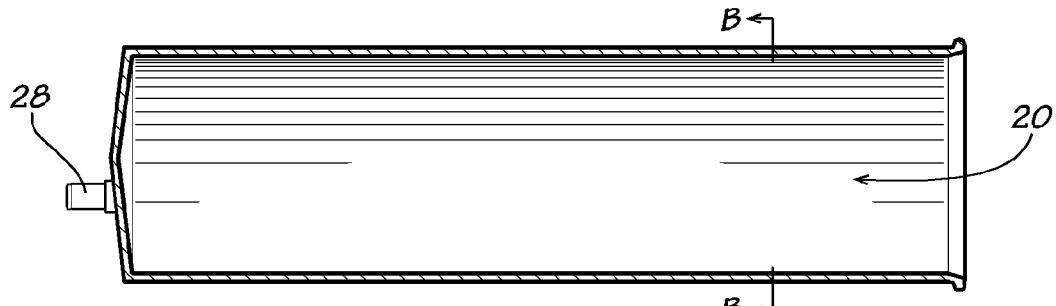
FIG. 10A is a first cross-sectional side view of the body of FIG. 2.
Figure 10B:
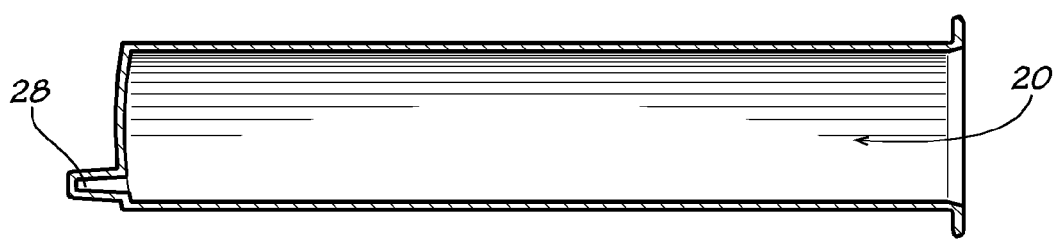
FIG. 10B is a second cross-sectional side view of the body of FIG. 10A.
Figure 10C:
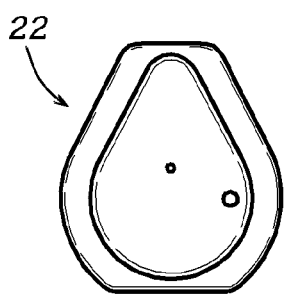
FIG. 10C is a top view of the body of FIG. 10B.
Figure 10D:
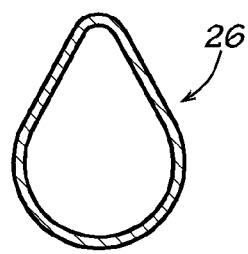
FIG. 10D is a cross-sectional view of the body of FIG. 10A taken at line B-B.
Figure 10E:
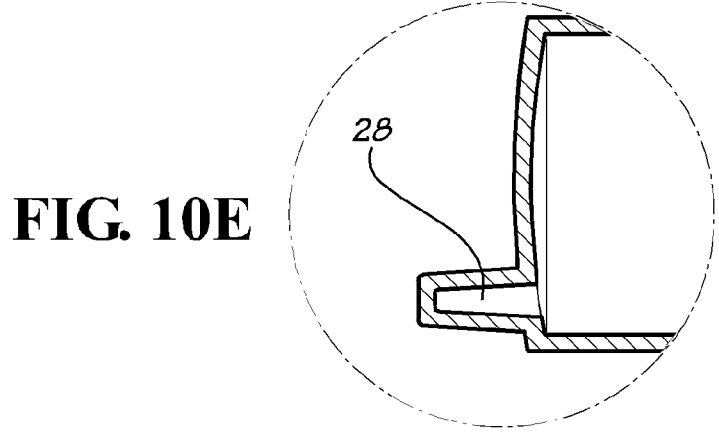
FIG. 10E is an enlarged cross-sectional side view of the distal end of the body of FIG. 10A.

FIGS. 10A-10E show a cross-sectional view of the syringe body 20 from a variety of angles. As shown in FIGS. 10B, 10C and 10E, the nipple 28 is positioned away from the central axis, which can be the cross-sectional center of gravity of the syringe 20.

Figure 11A:
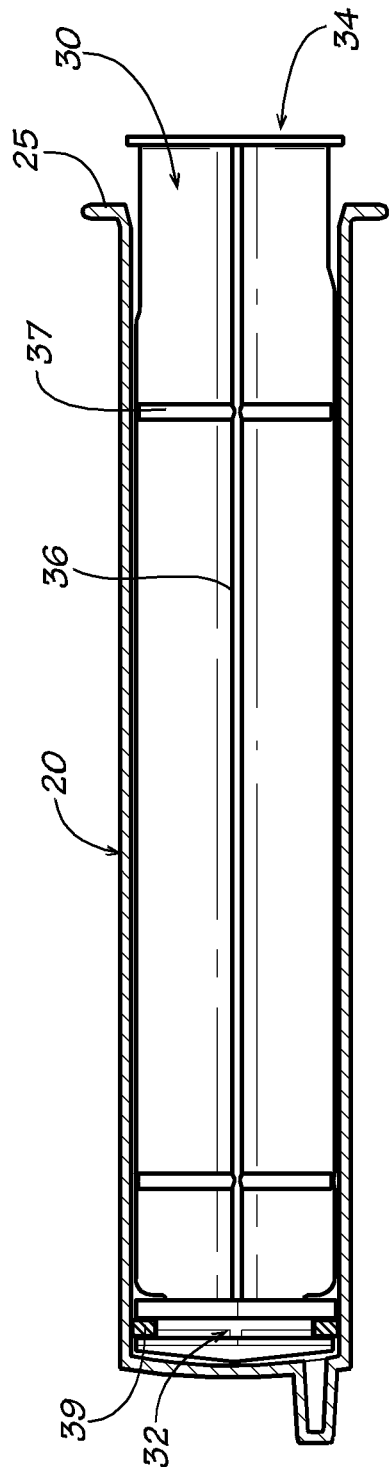
FIG. 11A is a cross-sectional side view of the enteral syringe of FIG. 2, shown with the plunger inserted into the body.
Figure 11B:
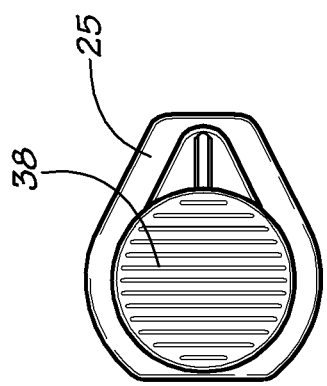
FIG. 11B is a top view of the enteral syringe of FIG. 11A.

In operation as additionally shown in FIGS. 11A-12B, the syringe 10 is loaded into a syringe pump (not shown) in which the distal end 22 of the syringe body is coupled to a fluid dispenser (not shown) and the proximal end 24 is coupled to a corresponding depressor (not shown) of the pump. FIG. 12A depicts the plunger 30 in a withdrawn state from within the body 20. FIG. 11A show the plunger 30 pushed toward the distal end of the body 20. The imaginary cross-sectional center of gravity is best exemplified with dashed lines in FIG. 12B. In preferred example embodiments, the semi-pointed end of the tear-drop shaped body is aligned along the horizontal axis of the pump and generally points towards the user. In this configuration, the tip 28 is towards the top of the syringe 10 as previously discussed. The rounded side of the tear-drop shaped body can rest within a track or other retaining mechanism of the syringe pump, which is typically designed to receive and secure circular-shaped syringes (as seen in FIG. 1). As a result, the syringe 10 of the present invention is able to maintain compatibility with the many known syringe pumps already in use throughout medical facilities across the world, while providing extra capacity to retain a larger quantity of dispensable fluid.

FIGS. 14A-14D depict a second example embodiment syringe having a syringe body 40 with a non-circular keyway shape and a correspondingly shaped plunger 46 to provide similar interaction as described in the embodiment depicted in FIGS. 2-9. As shown, the syringe body 40 has a rear carrier region 42 and a forward nose region 44. The rear carrier region 42 and the forward nose region 44 both have rounded perimeter edges. The rear carrier region 42 has a larger diameter than the forward nose region 44. The forward nose region 44 also has planar sides which taper from the rear carrier region 42.

FIGS. 15A-17B depict a self-venting enteral syringe 50 according to a third example embodiment of the present invention. In general, the enteral syringe 50 includes an elongated syringe body 52 and a plunger 60. The syringe body 52 defines an internal elongate cavity that stretches substantially along the length of the body from a proximal end 58 towards a distal end 53. In preferred example embodiments, the cavity mirrors, or substantially mirrors, the cross-section of the syringe body 52 providing a substantially constant outer-wall thickness of the same. The distal end 53 of the syringe body 52 comprises a nozzle or tip 55 in communication with the internal elongate cavity that is operable to be connected to one or more needles, hoses, and/or other implements as desired. In alternative embodiments, the syringe 50 can include two or more tips 55 to permit operational flexibility. In other embodiments, the syringe 50 can include three or more tips 55 or the tip(s) can be interchangeable. In still other embodiments, the one or more tips 55 can include a removable cap (not shown) to keep the contents of the syringe from leaking out before being connected to a needle, hose, etc.

The proximal end 58 of the syringe body 52 includes an opening for receiving the plunger 60 therein and also includes a flange 59 to provide a finger hold to permit manual operation by a user as is typical with known syringes or to engage a syringe pump. The syringe body 52 can have a substantially circular cross-section (as depicted in FIGS. 15A-17B), or can comprise a tear-drop, keyway, oval, elliptical, rectangular, or other non-circular or non-symmetrical cross-section (as depicted in FIGS. 18A-18D) as desired, and the opening generally has a cross-section that is sized and shaped to snugly receive an inserted complementary plunger 60 therein.

In example embodiments, the plunger 60 includes an elongated body 61 sized to be inserted into the opening of the syringe body 52, the body having a first distal end 64 and second proximal end 62. The distal end 64 comprises a sealing head 66 for tightly engaging an inner wall of the body cavity. As shown in FIGS. 15A-17B and discussed above, the sealing head and/or gasket 66 substantially mirrors the cross-section and diameter of the cavity to provide an appropriate seal between the head and the cavity. In example embodiments, the sealing head 66 frictionally engages the inner wall of the cavity, such that the plunger 60 remains in a particular position within the syringe body 52 absent user manipulation. The plunger body 61 also comprises at least one, and preferably two or more ribs 68 that extend to fit within the cross-section and/or diameter of the cavity (best seen in FIG. 17B). Thus, as the plunger 60 is selectively inserted into the cavity of the syringe body 52 and travels therein during use, the ribs 68 operate to keep the plunger 60 aligned within the cavity and prevent the plunger from tipping within the same. As such, the ribs 68 help maintain an adequate seal between the plunger head 66 and the wall of the cavity. At the proximal end 62 the plunger 60 includes a contact face to permit user manipulation of the syringe 50. In example embodiments, the contact face is circular in shape. Alternatively, the contact face can be any shape as desired.

In order to permit the syringe 50 of the present invention to be vented during use (and without fully removing the plunger 60 from the syringe body 52), the syringe body includes one or more vents 54 as shown in the drawing figures. The vents 54 selectively permit the transfer of air into the elongate syringe body cavity to prevent a vacuum from forming inside the same when in use. In depicted example embodiments, each vent 54 comprises a channel 56 that extends from the proximal end 58 a distance at least partially into the inner cavity of the syringe body 52. The length of the vents 54 is sufficient to extend beyond the seal or gasket of the syringe plunger while the plunger is retained in the syringe barrel in its retracted state, to allow air to pass through the vents around the seal. In alternative embodiments, the vent channel 56 extends from another outside surface of the syringe body 52 into the inner cavity. While example embodiments depicted in FIGS. 15A-17B depict four vents 54, alternative embodiments can include one vent, two vents, three vents, or five or more vents as desired.

FIGS. 18A-18D depict a self-venting enteral syringe 70 according to a fourth example embodiment of the present invention. The syringe 70, as depicted, has a non-circular non-symmetrical key-way cross-sectional syringe body 73 and plunger 74 that has a gasket 76 at the distal end. The body 73 and plunger 74 have similar elements and coordinate with each other in a similar manner to the embodiment described in FIGS. 14A-14D. The syringe 70 also includes similar characteristics, for example at least one vent 72, and operates through mechanics similar to the embodiment described in FIGS. 15A-17B.

FIGS. 19-23 show a second example plunger 124 according to an example embodiment of the present invention. The example plunger 124 can operate as the plunger in the embodiments described in FIGS. 2-18D. The plunger 124 has a proximal end 164 and a distal end 162. The distal end 162 includes a sealing head or gasket 166 that conforms to and forms a seal along the interior surface of a syringe body as described in FIGS. 2-18D. The plunger 124 further includes lower 146 and upper 144 ribs and a vertical flange 142, similar to the syringe described in FIGS. 2-18D. As shown the plunger 124 has a tear-dropped cross sectional profile, but can alternatively be designed to have a circular, elliptical, non-circular, non-symmetrical or key-way cross section as described in previous embodiments. The plunger 124 includes a fin or spine 170 that extends axially and perpendicular to the flange 142. First and second apertures 138, 134 extend through the spine 170 of the plunger 124. The apertures 138,134 provide support for supporting the syringe from an IV hanger or other support (best shown in FIGS. 22-23). In further alternate embodiments, the support feature can be part of the syringe barrel or a separate part connected to the syringe.

As depicted, a first aperture or cut-out 134 defines an axially elongated oval shape with parallel sides. This first cut-out 134 is transversely offset from the central axis (or cross-sectional center of gravity shown as an example in FIG. 12B) of the plunger 124, between the upper rib 144 and the lower rib 146. A second aperture or cut-out 138 has a more rounded oval shape with less elongated sides than the first cut-out 134. The second cut-out 138 is positioned along or adjacent the central axis (or cross-sectional center of gravity shown as an example in FIG. 12B) of the plunger 124, above the upper rib 144. In alternate embodiments of the invention, one, three or more apertures may be provided, and the position and configuration of the aperture(s) may vary.

Figure 22:
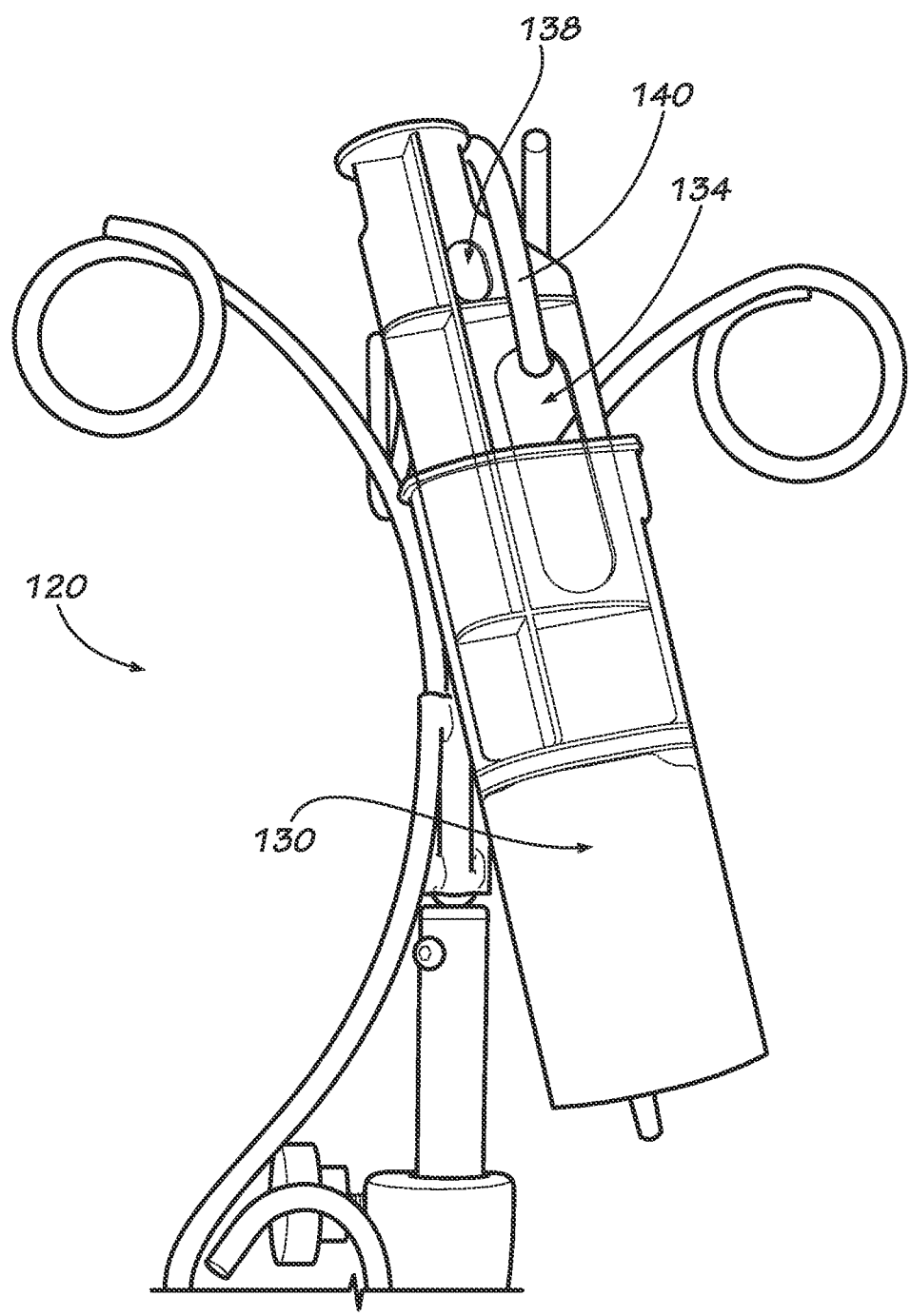
FIG. 22 is a perspective view of the plunger of FIG. 19, shown supporting a syringe body and hanging from a hook at a first angle.
Figure 23:
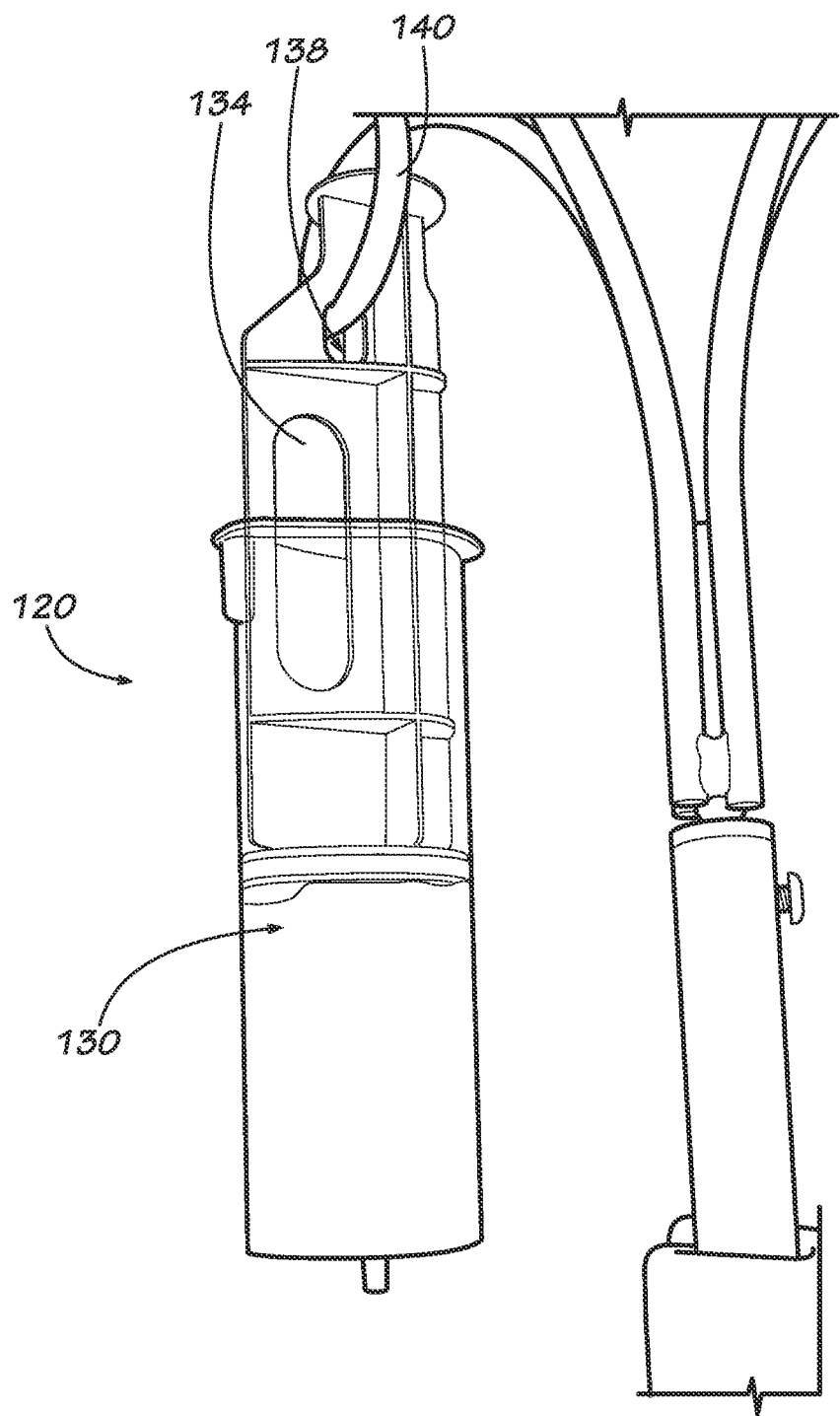
FIG. 23 is a perspective view of the plunger of FIG. 19, shown supporting a syringe body and hanging from a hook at a second angle.

In an example method of use, as depicted in FIGS. 22-23, a hook 140 from an IV stand can be inserted through either the first cut-out 138 or the second cut-out 134 as the plunger 124 is secured within a syringe body 130. When the IV hook 140 is inserted through the first cut-out 138, the syringe 120 hangs in a substantially vertical orientation (as shown in FIG. 23); and when the IV hook 140 is inserted through the second cut-out 134, the syringe 120 hangs at an oblique angle relative to vertical (as shown in FIG. 24). In this manner, the angular orientation of the hanging syringe can be selectively varied to control the discharge and draining from the syringe, as well as the orientation of the syringe vent(s) if provided, when in use.

All of the components discussed and embodiments described herein can be formed from a variety of materials as desired by a user. In example embodiments, the syringe can be formed from plastics (i.e. polypropylene), other polymers, glass, metals, metal alloys, resins, rubbers, rubber derivatives, elastomerics (i.e. santoprene), silicones or other known materials. In commercial embodiments, the syringe body is formed from polypropolene, the plunger is formed from the same, and the sealing head is formed from an elastomeric. Optionally, color additives may be added to provide protection from UV light and/or colorants may be added to the syringe as desired and/or to identify certain properties/characteristics (i.e. administration path) or contents. In alternative embodiments, the syringe can include external markings to indicate volume capacity and remaining content levels.

While the invention has been described with reference to preferred and example embodiments, it will be understood by those skilled in the art that a variety of modifications, additions and deletions are within the scope of the invention, as defined by the following claims.

What is claimed is:

1. A syringe comprising:
  a syringe body defining an elongate cavity therein, the elongate cavity having a substantially continuous cross-sectional internal profile along a lengthwise dimension thereof, the cross-sectional internal profile having a first radiused portion with a larger radius of curvature at a first end, and a second radiused portion having a smaller radius of curvature at an opposite second end, the cross-sectional internal profile further comprising two opposed sides tapering generally inwardly from the larger radius of curvature to the smaller radius of curvature between the first end and the second ends; and
  a syringe plunger at least partially mounted within the elongate cavity of the syringe body for translational advancement and retraction therein, the plunger comprising a sealing head for mating engagement within the elongate cavity of the syringe body and having a cross-sectional external profile substantially matching the cross-sectional internal profile of the elongate cavity of the syringe body.

2. The syringe of claim 1, wherein the cross-sectional internal profile of the elongate cavity of the syringe body and the cross-sectional external profile of the syringe plunger sealing head are substantially tear-drop shaped.

3. The syringe of claim 1, wherein the cross-sectional internal profile of the elongate cavity of the syringe body and the cross-sectional external profile of the syringe plunger sealing head are key-way shaped.

4. The syringe of claim 1, wherein the syringe body comprises at least one vent channel extending from the elongate cavity to outside of the syringe body.

5. The syringe of claim 4, wherein the at least one vent channel permits external airflow past the syringe plunger sealing head when the syringe plunger is in a retracted position in the elongate cavity but external airflow is not permitted past the syringe plunger sealing head when the syringe plunger is in an advanced position in the elongate cavity.

6. The syringe of claim 1, further comprising at least one support feature for hanging the syringe from a support structure.

7. The syringe of claim 6, wherein the at least one support feature comprises an aperture extending through the plunger.

8. The syringe of claim 6, wherein the at least one support feature comprises a first support feature configured for hanging the syringe at a first angle with respect to vertical, and a second support feature configured for hanging the syringe at a second angle different from the first angle with respect to vertical.

9. A syringe comprising:
  a syringe body defining an elongate cavity therein, the elongate cavity defining a substantially tear-drop shaped cross-sectional internal profile having a first radiused portion having a larger radius of curvature at a first end of the tear-drop shaped cross-sectional internal profile and a second radiused portion having a smaller radius of curvature at an opposite second end of the tear-drop shaped cross-sectional internal profile, and opposed sides tapering substantially linearly inwardly from the larger radius of curvature to the smaller radius of curvature between the first end and the second end; and
  a syringe plunger mounted within the elongate cavity of the syringe body for translational advancement and retraction therein, the plunger having a sealing head for mating engagement within the substantially tear-drop shaped cross-sectional internal profile of the elongate cavity of the syringe body and having a substantially tear-drop shaped cross-sectional external profile substantially matching the cross-sectional internal profile of the elongate cavity of the syringe body.

10. The syringe of claim 9, wherein the syringe body comprises at least one vent channel extending from the elongate cavity to outside of the syringe body.

11. The syringe of claim 10, wherein the at least one vent channel permits external airflow past the syringe plunger sealing head when the syringe plunger is in a retracted position in the elongate cavity but external airflow is not permitted past the syringe plunger sealing head when the syringe plunger is in an advanced position in the elongate cavity.

12. The syringe of claim 9, further comprising at least one support feature for hanging the syringe from a support structure.

13. The syringe of claim 12, wherein the at least one support feature comprises an aperture extending through the plunger.

14. The syringe of claim 12, wherein the at least one support feature comprises a first support feature configured for hanging the syringe at a first angle with respect to vertical, and a second support feature configured for hanging the syringe at a second angle different from the first angle with respect to vertical.

15. A syringe comprising:
a syringe body defining an elongate cavity therein, the elongate cavity defining a substantially key-way shaped cross-sectional internal profile having a first radiused portion having a larger radius of curvature at a first end of the key-way shaped cross-sectional internal profile and a second radiused portion having a smaller radius of curvature at an opposite second end of the key-way shaped cross-sectional internal profile, and opposed sides tapering generally inwardly from the larger radius of curvature to the smaller radius of curvature between the first end and the second end, at least one of the opposed sides defining an inwardly concave radius of curvature; and
a syringe plunger mounted within the elongate cavity of the syringe body for translational advancement and retraction therein, the plunger having a sealing head for mating engagement within the substantially key-way shaped cross-sectional internal profile of the elongate cavity of the syringe body and having a substantially key-way shaped cross-sectional external profile substantially matching the cross-sectional internal profile of the elongate cavity of the syringe body.

16. The syringe of claim 15, wherein both of the opposed sides define substantially symmetric inwardly concave radii of curvature.

17. The syringe of claim 15, wherein the syringe body comprises at least one vent channel extending from the elongate cavity to outside of the syringe body.

18. The syringe of claim 17, wherein the at least one vent channel permits external airflow past the syringe plunger sealing head when the syringe plunger is in a retracted position in the elongate cavity but external airflow is not permitted past the syringe plunger sealing head when the syringe plunger is in an advanced position in the elongate cavity.

19. The syringe of claim 15, further comprising at least one support feature for hanging the syringe from a support structure.

20. The syringe of claim 19, wherein the at least one support feature comprises an aperture extending through the plunger.

21. The syringe of claim 19, wherein the at least one support feature comprises a first support feature configured for hanging the syringe at a first angle with respect to vertical, and a second support feature configured for hanging the syringe at a second angle different from the first angle with respect to vertical.

* * * * *